United States Patent
Hansen et al.

(10) Patent No.: US 10,105,243 B2
(45) Date of Patent: *Oct. 23, 2018

(54) ANKLE-FOOT PROSTHESIS FOR AUTOMATIC ADAPTATION TO SLOPED WALKING SURFACES

(71) Applicants: U.S. Department of Veterans Affairs, Washington, DC (US); Regents of the University of Minnesota, Minneapolis, MN (US)

(72) Inventors: Andrew H. Hansen, Apple Valley, MN (US); Eric A. Nickel, Brooklyn Park, MN (US)

(73) Assignees: U.S. Department of Veterans Affairs, Washington, DC (US); Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/359,242

(22) Filed: Nov. 22, 2016

(65) Prior Publication Data

US 2017/0071761 A1    Mar. 16, 2017

Related U.S. Application Data

(63) Continuation of application No. 14/022,645, filed on Sep. 10, 2013, now Pat. No. 9,549,827.

(Continued)

(51) Int. Cl.
*A61F 2/50* (2006.01)
*A61F 2/66* (2006.01)
*A61F 2/74* (2006.01)

(52) U.S. Cl.
CPC .... *A61F 2/6607* (2013.01); *A61F 2002/5006* (2013.01); *A61F 2002/6642* (2013.01); *A61F 2002/745* (2013.01); *A61F 2002/748* (2013.01)

(58) Field of Classification Search
CPC .......... A61F 2/604; A61F 2/6607; A61F 2/66; A61F 2002/5003; A61F 2002/5006;
(Continued)

(56) References Cited

U.S. PATENT DOCUMENTS 2,843,853 A   7/1958 Mauch
4,923,475 A   5/1990 Gosthnian et al.
(Continued)

FOREIGN PATENT DOCUMENTS

WO   WO 2008/048658 A2   4/2008
WO   WO 2011/129892 A2   10/2011
WO   WO 2012/099709 A2   7/2012

OTHER PUBLICATIONS

Hansen, A., Childress, D., Miff, S., Gard, S., Mesplay, K. (2004) The Human Ankle During Walking: Implications for Design of Biomimetic Ankle Prostheses and Orthoses. Journal of Biomechanics, vol. 37, No. 10, 1467-1474.
(Continued)

*Primary Examiner* — Thomas J Sweet
*Assistant Examiner* — Christie Bahena
(74) *Attorney, Agent, or Firm* — Ballard Spahr LLP

(57) ABSTRACT

An ankle-foot prosthesis includes a foot plate, an ankle frame attached to the foot plate, a yoke pivotally connected to the ankle frame and including a member for attaching to a leg, a damper having a first end connected to the yoke and a second end connected to the ankle frame, and a control mechanism for switching the damper between low and high settings.

20 Claims, 16 Drawing Sheets

Related U.S. Application Data

(60) Provisional application No. 61/703,799, filed on Sep. 21, 2012, provisional application No. 61/851,740, filed on Mar. 13, 2013.

(58) Field of Classification Search
CPC ...... A61F 2002/5007; A61F 2002/5033; A61F 2002/5035; A61F 2002/5073; A61F 2002/604; A61F 2002/6692; A61F 2002/6685; A61F 2002/6678; A61F 2002/6671; A61F 2002/6664; A61F 2002/6657; A61F 2002/665; A61F 2002/6642; A61F 2002/6635; A61F 2002/6621; A61F 2002/6614; A61F 2002/74; A61F 2002/745; A61F 2002/748; B25J 9/0006
See application file for complete search history.

(56) References Cited

U.S. PATENT DOCUMENTS

| | | | |
|---|---|---|---|
| 5,367,790 | A | 11/1994 | Gamow et al. |
| 5,458,143 | A | 10/1995 | Herr |
| 5,701,686 | A | 12/1997 | Herr et al. |
| 6,029,374 | A | 2/2000 | Herr et al. |
| 6,443,993 | B1 | 9/2002 | Koniuk |
| 6,610,101 | B2 | 8/2003 | Herr et al. |
| 6,764,520 | B2 | 7/2004 | Deffenbaugh et al. |
| 7,295,892 | B2 | 11/2007 | Herr et al. |
| 7,313,463 | B2 | 12/2007 | Herr et al. |
| 7,785,373 | B2 | 8/2010 | Frye, Jr. |
| 7,942,935 | B2 | 5/2011 | Iversen et al. |
| 7,985,265 | B2 | 7/2011 | Moser et al. |
| 8,048,172 | B2 | 11/2011 | Jonsson et al. |
| 8,376,971 | B1 | 2/2013 | Herr et al. |
| 8,480,760 | B2 | 7/2013 | Hansen et al. |
| 8,597,369 | B2 | 12/2013 | Hansen et al. |
| 8,696,764 | B2 | 4/2014 | Hansen et al. |
| 8,764,850 | B2 | 7/2014 | Hansen et al. |
| 8,888,864 | B2 | 11/2014 | Iversen et al. |
| 2003/0120354 | A1 | 6/2003 | Doddroe et al. |
| 2004/0064195 | A1 | 4/2004 | Herr |
| 2005/0070834 | A1 | 3/2005 | Herr et al. |
| 2005/0137717 | A1 | 6/2005 | Gramnas et al. |
| 2006/0069448 | A1 | 3/2006 | Yasui |
| 2006/0235544 | A1 | 10/2006 | Iversen et al. |
| 2006/0241782 | A1 | 10/2006 | Curtis |
| 2007/0027555 | A1 | 2/2007 | Palmer et al. |
| 2007/0043449 | A1 | 2/2007 | Herr et al. |
| 2008/0300692 | A1 | 12/2008 | Moser et al. |
| 2008/0306612 | A1 | 12/2008 | Mosler |
| 2010/0185301 | A1 | 7/2010 | Hansen et al. |
| 2012/0130508 | A1 | 5/2012 | Harris et al. |

OTHER PUBLICATIONS

Williams RJ, Hansen AH, Gard SA. (2009) Prosthetic Ankle-Foot Mechanism Capable of Automatic Adaptation to the Walking Surface. Journal of Biomechanical Engineering, vol. 131, No. 3, 035002 (7 pgs).

Hansen A, Brielmaier S, Medvec J, Pike A, Nickel E, Merchak P, Weber M (2012) Prosthetic Foot with Adjustable Stability and its Effects on Balance and Mobility. 38th Annual Meeting and Scientific Symposium of the American Academy of Orthotists and Prosthetists, Mar. 21-24, Atlanta, Georgia (1 pg).

Nickel EA, Hansen AH, Gard SA. (2012) Prosthetic Ankle-Foot System that Adapts to Sloped Surfaces. ASME Journal of Medical Devices, vol. 6, No. 1, 011006 (6 pgs).

PCT International Search Report and the Written Opinion in International App. No. PCT/US2014/023141 dated Jun. 27, 2014 (11 pp.).

Biomechantronics-Powered Ankle-Foot Prostheses. http://biomech.media.mit.edu/portfolio_page/powered-ankle-foot-prostheses/ (2 pages). Accessed Jan. 13, 2015.

Biomechantronics-Running Powered Ankle-Foot Prostheses. http://biomech.media.mit.edu/ (2 pages). Accessed Jan. 13, 2015.

J. Markowitz, P. Krishnaswamy, M. F. Eilenberg, K. Endo, C. Barnhart, and H. M. Herr. *Speed adaptation in a powered transtibial prosthesis controlled with a neuromuscular model*, Philosophical Transactions of the Royal Society B: Biological Sciences, vol. 366. No. 1570, pp. 1621-1631, 2011.

M. F. Eilenberg, H. Geyer, and H. M. Herr. *Control of a powered ankle-foot prosthesis based on a neuromuscular model*, IEEE Transactions on Neural Systems and Rehabilitation Engineering, vol. 18. No. 2, pp. 164-173, 2010.

S. Au, J. Weber, and H.M Herr. *Powered Ankle-Foot Prosthesis Improves Walking Metabolic Economy*, IEEE Transactions on Robotics, vol. 25, No. 1, pp. 51-66, 2009.

S. K. Au, M. Berniker, and H. M. Herr. *Powered ankle-foot prosthesis to assist level-ground and stair-descent gaits*, Neural Networks, vol. 21, pp. 654-666, 2008.

S. K. Au, and H. M. Herr. *Powered ankle-foot prosthesis*, IEEE Robotics & Automation Magazine, vol. 15, No. 3, pp. 52-59, 2008.

H. Herr, J. Weber, and S. Au. *Powered ankle-foot prosthesis*, Biomechanics of the Lower Limb in Health, Disease and Rehabilitation, pp. 72-74, Sep. 3-5, 2007.

E. C. Martinez-Villalpando, H. M. Herr. *Estimation of ground reaction force and zero moment point on a powered ankle-foot prosthesis*, IEEE Engineering in Medicine and Biology International Conference, Lyon, France, Aug. 23-26, 2007, pp. 4687-4692, 2007.

S. K. Au, J. Weber, H. M. Herr and E.C. Martinez-Villapando, *Powered ankle-foot prosthesis for the improvement of amputee ambulation*, IEEE Engineering in Medicine and Biology International Conference, Lyon, France, Aug. 23-27, 2007, pp. 3020-3026, 2007.

S. K. Au, J. Weber, and H. Herr. *Biomechanical design of a powered ankle-foot prosthesis*, IEEE 10th International Conference on Rehabilitation Robotics, Jun. 12-15, 2007, The Netherlands, pp. 298-303, 2007.

Biomechatronics—Publications. http://biomech.media.mit.edu/ (7 pages). Accessed Feb. 5, 2014.

Mobbili. Derwent Abstract of WO 2011/117033. Sep. 29, 2011 A61F2/6607.

ANKLE-FOOT PROSTHESIS FOR AUTOMATIC ADAPTATION TO SLOPED WALKING SURFACES

CROSS-REFERENCE TO RELATED APPLICATIONS

This is a continuation application of U.S. application Ser. No. 14/022,645, filed Sep. 10, 2013, which claims priority based on prior two (2) U.S. Provisional Application Ser. No. 61/703,799, filed Sep. 21, 2012, and Ser. No. 61/851,740, filed Mar. 13, 2013, both hereby incorporated herein in their entirety by reference. The present application is further related to International Application No. PCT/US2007/022208, filed Oct. 17, 2007 (WO 2008/048658, Apr. 24, 2008) (U.S. application Ser. No. 12/311,818, filed Apr. 13, 2009, Published as US 2010/0185301, on Jul. 22, 2010), U.S. application Ser. No. 12/462,056, filed Jul. 28, 2009 (Published as US 2010/0030343, on Feb. 4, 2010), U.S. application Ser. No. 13/066,361, filed Apr. 12, 2011 (Published as US 2012/0016493, on Jan. 19, 2012), U.S. application Ser. No. 13/374,881, filed Jan. 20, 2012 (Published as US 2013/0006386, on Jan. 3, 2013), and International Application No. PCT/US2011/000675, filed Apr. 4, 2011 (WO 2011/129892, Oct. 20, 2011), all of which are hereby incorporated herein in their entirety by reference.

FIELD AND BACKGROUND OF THE INVENTION

The present invention is generally directed to prosthetic and orthotic devices, and more particularly to an ankle-foot prosthesis for automatic adaptation to level, as well as sloped walking surfaces. Even more particularly, the invention is directed to a device or system for use by lower limb amputees to more easily and safely walk over a variety of sloped terrain, as well as to provide more stability during standing and swaying tasks.

Most currently available prosthetic ankle devices are spring-like structures that operate about one equilibrium point (i.e., one resting angle). These systems can work nicely on level terrain but cause instabilities when lower limb prosthesis users walk on sloped surfaces. Many systems have been described that use hydraulic dampers and/or variations of damping to adjust the properties of the prosthesis (Mauch, 1958—U.S. Pat. No. 2,843,853; Koniuk, 2002—U.S. Pat. No. 6,443,993; Moser et al, 2011—U.S. Pat. No. 7,985,265), including the use of microprocessor-control to adjust damping properties. The inherent problem with damping control of the ankle is the associated loss of energy that occurs. One system exists that uses a motor to change the equilibrium point of a spring-like prosthetic foot (Jonsson et al, 2011—U.S. Pat. No. 8,048,172). However, this system requires multiple steps on a new terrain before it is able to adapt to the new slope. A more desirable system would adapt to different sloped surfaces on each and every step of walking. Lastly, powered ankle-foot systems are being developed (Hugh Herr, Massachusetts Institute of Technology; Thomas Sugar, Arizona State University; Michael Goldfarb, Vanderbilt University). These systems all actively push the prosthesis user with a motor during various times in the gait cycle and require large power sources, e.g., heavy batteries and motors. The only currently available system on the market (iWalk BiOM) is expensive, making it impractical for the majority of lower limb prosthesis users. Also, the high power requirements necessitate carrying additional batteries and frequent charging of batteries.

ASPECTS OF THE INVENTION

The present disclosure is directed to various aspects of the present invention.

One aspect of the present invention is to provide an ankle-foot prosthesis that allows a user to have a more natural, and thus more comfortable gait.

Another aspect of the present invention is to provide an ankle-foot prosthesis that is more energy-efficient when used for walking or other gait.

Another aspect of the present invention is to provide an ankle-foot prosthesis that is simple in design and construction and, thus, uses fewer parts or components, and requires no or low maintenance.

Another aspect of the present invention is to provide an ankle-foot prosthesis that is compact and more durable than, for example, those using multitude of mechanical parts leading to a higher rate of failure.

Another aspect of the present invention is provide an ankle-foot prosthesis that resists or prevents undesirable backward swing, which could lead to imbalance or injury.

Another aspect of the present invention is to provide an ankle-foot prosthesis that is quieter, light-weight, and less clumsy to use, and thus more user-friendly.

Another aspect of the present invention is to provide an ankle-foot prosthesis that automatically adapts to different sloped walking surfaces on every step of walking.

Another aspect of the present invention is to provide an ankle-foot prosthesis that can easily switch into a stable mode for standing or swaying, for example, when washing the dishes.

Another aspect of the present invention is to provide an ankle-foot prosthesis, which includes a foot plate, an ankle frame attached to the foot plate, a yoke pivotally connected to the ankle frame and including a member for attaching to a leg, a damper having a first end connected to the yoke and a second end connected to the ankle frame, and a control mechanism for switching the damper between low and high settings.

Another aspect of the present invention is to provide an ankle-foot prosthesis, which includes a foot plate, an ankle frame attached to the foot plate and including anterior and posterior portions and an apex portion, a yoke pivotally connected to the apex portion of the ankle frame and including a member for attaching to a leg, a hydraulic damper having a first end pivotally connected to the yoke and a second end connected to the posterior portion of the ankle frame; a spring disposed in parallel to the damper, and a control mechanism for controlling extension and compression of the damper.

Another aspect of the present invention is to provide a method of using an ankle-foot prosthesis by an amputee, which includes a) providing an ankle-foot prosthesis including i) a foot plate, ii) an ankle frame attached to the foot plate, iii) a yoke pivotally connected to the ankle frame and including a member for attaching to a leg, iv) a damper having a first end connected to the yoke and a second end connected to the ankle frame, and v) a control mechanism for switching the damper between low and high settings to selectively control extension, compression, or both extension and compression thereof; b) attaching the ankle-foot prosthesis to a lower limb of the amputee; c) allowing the amputee to ambulate for at least one gait cycle, wherein the gait cycle includes i) the ankle-foot prosthesis in an initial neutral position to a first plantarflexion position such that the foot plate is substantially flat on a walking surface, and ii) the ankle-foot prosthesis in a toe-off plantarflexion position; d) switching the damper to the high extension setting substantially at the first plantarflexion position; and e) switching the damper to the low extension setting substantially at the toe-off plantarflexion position.

In summary, the present invention is directed to a prosthetic ankle-foot device that can automatically adapt its function for walking on different sloped surfaces, allowing its user to walk on these surfaces with more stability and confidence. The invention also provides a stable mode for standing and swaying tasks (e.g., washing the dishes).

BRIEF DESCRIPTION OF THE DRAWINGS

One of the above and other aspects, novel features and advantages of the present invention will become apparent from the following detailed description of the non-limiting preferred embodiment(s) of invention, illustrated in the accompanying drawings, wherein.

DETAILED DESCRIPTION OF THE PREFERRED EMBODIMENT(S) OF THE INVENTION

Figure 1:
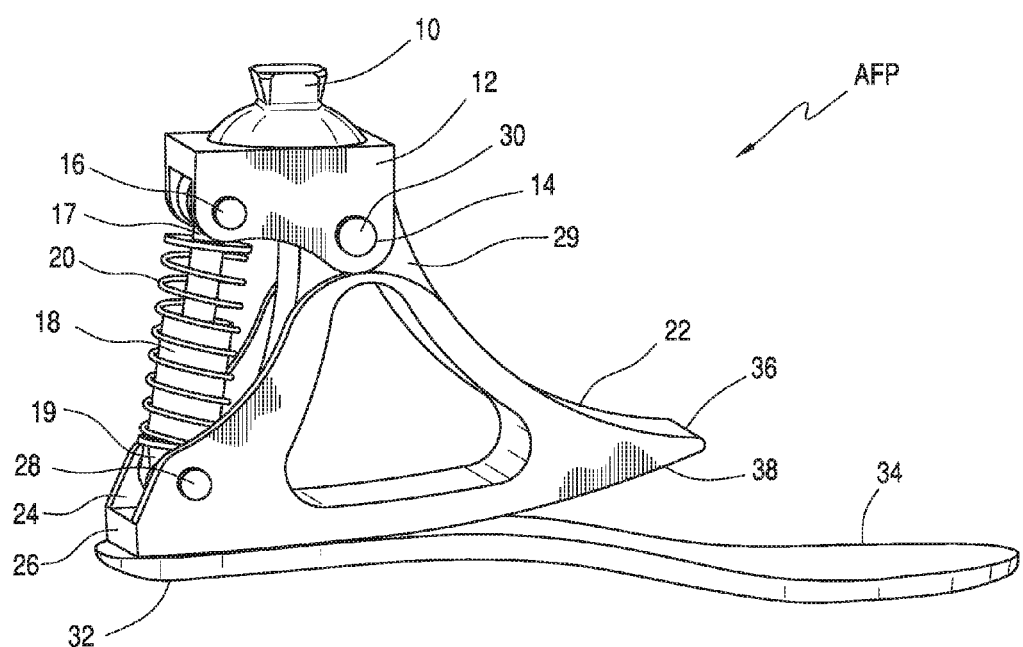
FIG. 1 is a perspective view of a preferred embodiment of the ankle-foot prosthesis in accordance with the present invention.
Figure 2:
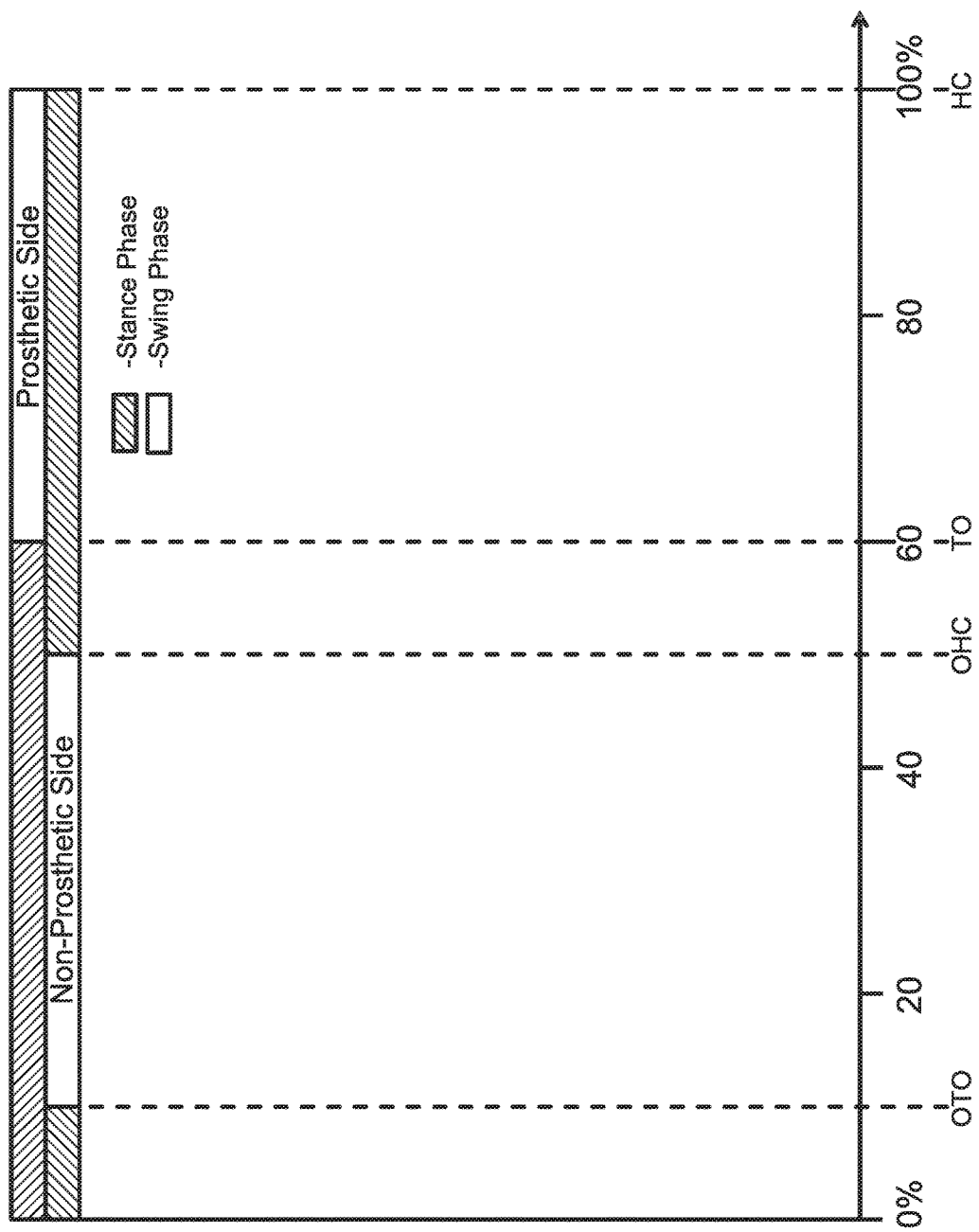
FIG. 2 illustrates a blank timing plot for the ankle-foot prosthesis of the present invention, which can be used to create any gait cycle that begins with prosthetic heel contact (HC) and continues until the next HC (100% of the gait cycle)

Referring to FIG. 1, a preferred embodiment of the ankle-foot prosthesis AFP will be described. As shown, a generally pyramid-like attachment part 10, consistent with standard endoskeletal componentry in prosthetics, is provided at the top of a yoke 12, on the opposite ends of which are holes drilled for front and rear pivotal attachments 14 and 16, respectively. The rear pivot 16 attaches to one end 17 of a preferably microprocessor controlled damper device 18 (to be described in more detail below). A neutralizing spring 20 is connected in parallel to the damper 18, such that its length change is equal to that of the damper.

The damper device 18 attaches on its other end 19 to an ankle frame 22, which has a yoke opening 24 and holes drilled at its posterior end 26 to pivotally attach to the damper 18 using a shaft 28. The "ankle" of the device AFP is a shaft 30 connecting the yoke 12 with the apex 29 of the ankle frame 22.

The ankle frame 22 attaches with one or more bolts (or other suitable fixation means) to the rear portion 32 of a flexible, yet deflectable rigid foot plate 34. The anterior end 36 of the ankle frame 22 includes a follower or upwardly inclined surface 38 that limits the deflection of the foot plate 34, such that the ankle-foot device AFP will take a biomimetic ankle-foot roll-over shape during walking. The geometry of the surface 38 is such that it provides the correct roll-over shape when the "ankle" is locked into a plantarflexed angle at the time of foot flat of walking, i.e., an angle of about 10 to 15 degrees.

The damper 18 is designed to have different values for compression and extension damping that can be controlled by using a suitable microprocessor (not shown). Specifically, the microprocessor would have the capability to variably manage the timing for opening and closing the valves and the variable restriction element, shown in FIG. 7 and described below in more detail. For walking, the compression damping is set to a very low level and is unchanged throughout the gait cycle. The extension damping for walking is set to a very high level at the beginning of the gait cycle and changes to a very low level damping at the time of toe-off (which must be sensed using one or more sensors of force, acceleration, or other properties). The extension damping can remain at a low level of damping for at least the time needed to return the ankle to a neutral or dorsiflexed position for swing phase and at most the time to the next foot flat event of the prosthesis. For standing, both compression and extension damping levels can be controlled to be very high, providing a flatter effective shape and increasing the stability of the prosthesis user.

For a normal gait cycle, the heel of the system, shown in FIG. 1, will contact the surface and the foot will "find the surface" under a low stiffness of the neutralizing spring 20. The compression damping is low so the ankle reacts primarily in this phase of gait to the neutralizing spring 20. The compression damping could be altered for different patients, but would be static throughout the gait cycle once set by the prosthetist or the user. After foot flat, the ankle is at a maximally plantarflexed position and would normally start to dorsiflex. In this invention, the extension damping would be very high, essentially locking the ankle in a plantarflexed position. As the person rolls over the device, the flexible footplate 34 flexes up to the follower 38, producing a biomimetic ankle-foot roll-over shape. After the opposite foot contacts the ground, energy is returned from the flexible footplate 34 and the ankle goes into late stance plantarflexion (the angle at which it was set to at foot flat). As the prosthetic device leaves the walking surface (toe-off), the extension damping switches a very low level, allowing the neutralizing spring 20 to bring the ankle back to a neutral or slightly dorsiflexed position, which allows for toe clearance during the swing phase. The damping level needs to be low enough to allow the ankle to return to neutral during the first third or half of the swing phase. After the ankle has returned to neutral or a slightly dorsiflexed position and before the prosthesis gets to foot flat on the next cycle, the extension damping should shift to a very high level for the next cycle.

The operation of the ankle in the manner described above, allows the foot to "find the surface" during walking. For uphill walking, the foot finds the surface in a more dorsiflexed position compared with that for level walking and thus the equilibrium point of the ankle is set in more dorsiflexion. For downhill walking, the foot finds the surface in a more plantarflexed position compared with that for level walking. In this way, the ankle-foot device automatically adapts to different terrain on each and every step of walking. Also, the control mechanism for the ankle would be relatively simple in that it only changes the extension damping of the damper 18 between two levels during walking. The control mechanism also needs to determine when the ankle-foot system is in "walking" and "standing" modes and switch its behavior. For "standing" mode, the damping for both compression and extension of the damper 18 should be set to very high, as mentioned earlier.

Referring to FIGS. 2-6, various timing plots for the ankle-foot prosthesis AFP of the invention will now be described. The blank plot of FIG. 2 can be used to create any gait cycle that begins with prosthetic heel contact (HC) and continues until the next HC (100% of the gait cycle). For the first 10% of the gait cycle, both feet are on the ground as weight transitions from the opposite limb to the prosthetic limb. At approximately 10%, the opposite toe is lifted from the floor (opposite toe-off or OTO). When the opposite toe is off the ground, only the prosthetic foot is in contact with the walking surface and supporting the weight of the body, so this is considered prosthetic single-limb-support (40% of the gait cycle). This also corresponds to the period of highest load on the prosthetic limb as the user rolls over their foot. At approximately 50% of the gait cycle, the opposite heel contacts the surface (OHC) and weight begins to transition from the prosthetic limb to the sound limb. At approximately 60% of the gait cycle, the prosthetic limb is lifted off the surface (toe-off or TO) and the remainder of the gait cycle is sound side single limb support as the prosthetic limb swings through. (These numbers are approximate.) Modern conventional usages are changing to use Initial Contact, instead of Heel Contact, because the heel is not always the first part of the foot to come into contact with the walking surface (such as persons with drop-foot syndrome or equinus deformity), but for this invention the two should be equivalent.

Figure 3:
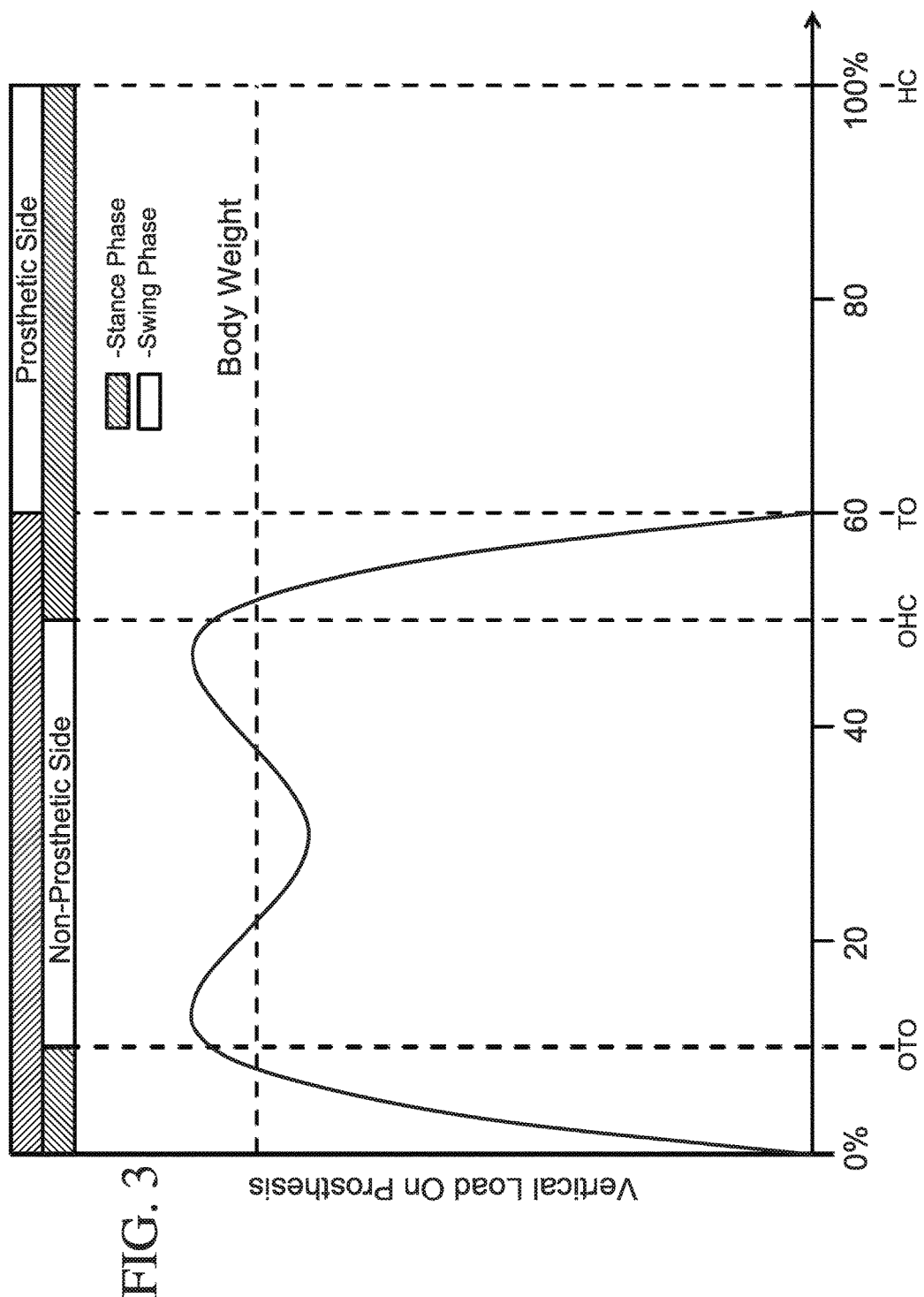
FIG. 3 illustrates a plot of the theoretical vertical load on the prosthesis.

FIG. 3 illustrates a plot of the theoretical vertical load on the prosthesis. The plot shows the standard double-hump shape of the vertical component of the ground reaction force vector from standard gait analyses. The first peak corresponds to load acceptance on the prosthetic side, where the prosthesis is used to brake the descent of the body center of mass. The second peak occurs as the user pushes off of their prosthetic side and begins to transition onto their sound side (and occurs around opposite heel contact (OHC). The vertical load drops to 0 as the toe leaves the surface (toe-off, TO) and remains there through swing phase. During single limb support, the vertical load can reach levels that are greater than body weight. For slow walking, the peak load could be 1.1×BW (Body Weight), whereas for fast walking or sudden stumbles the peak load could be upwards of 1.5×BW (Body Weight).

Figure 4:
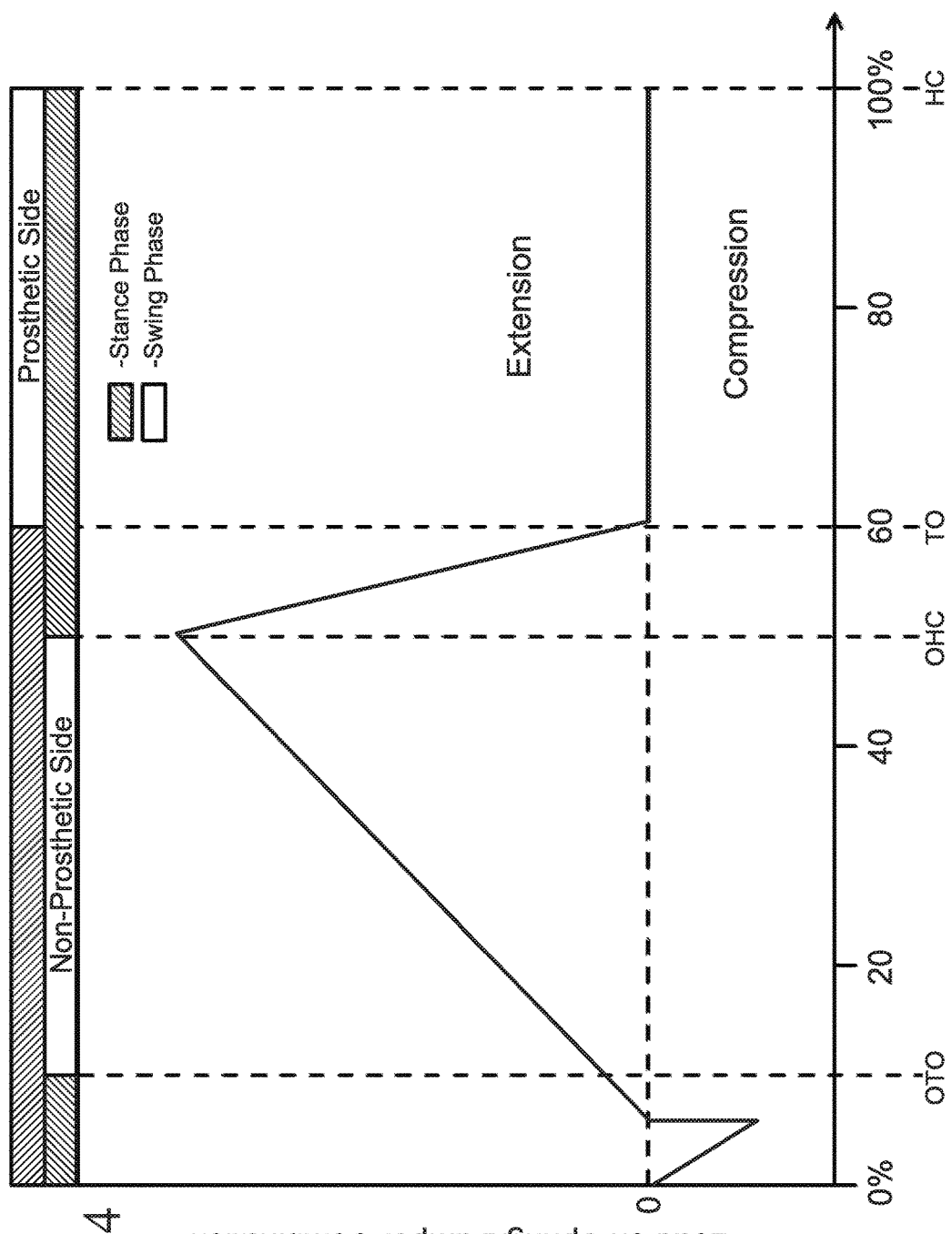
FIG. 4 illustrates a plot of the load on spring/damper combination at the start of stance phase, the heel of the prosthesis making contact with the surface, placing a compressive load on the spring/damper combination.

FIG. 4 illustrates a plot of the load on the spring/damper combination at the start of stance phase, the heel of the prosthesis making contact with the surface, placing a compressive load on the spring/damper combination. This load continues until the foot is resting flat against the walking surface. At that time, the user begins to roll over their prosthetic foot. The damper is set to a high extension damping level, so it does not extend, thus the spring becomes an internal stress and when the user starts to roll over their foot, the compressive load very rapidly switches to a small tensile load and then the tensile load gradually increases as the user rolls over the foot. Near the end of stance phase, the user has rolled over the prosthesis and begins to lift the foot from the ground, reducing the tensile force on the spring-damper combination, until the toe is lifted from the surface. At this point the spring is still applying an internal force within the system but is unable to actuate motion because the damper is still in a high extension damping state and resists the spring. When the load is removed, the hydraulic cutoff valve (fluid equivalent of a switch) is opened allowing the spring to extend and quickly return the foot to a neutral ankle position for swing phase.

Figure 5:
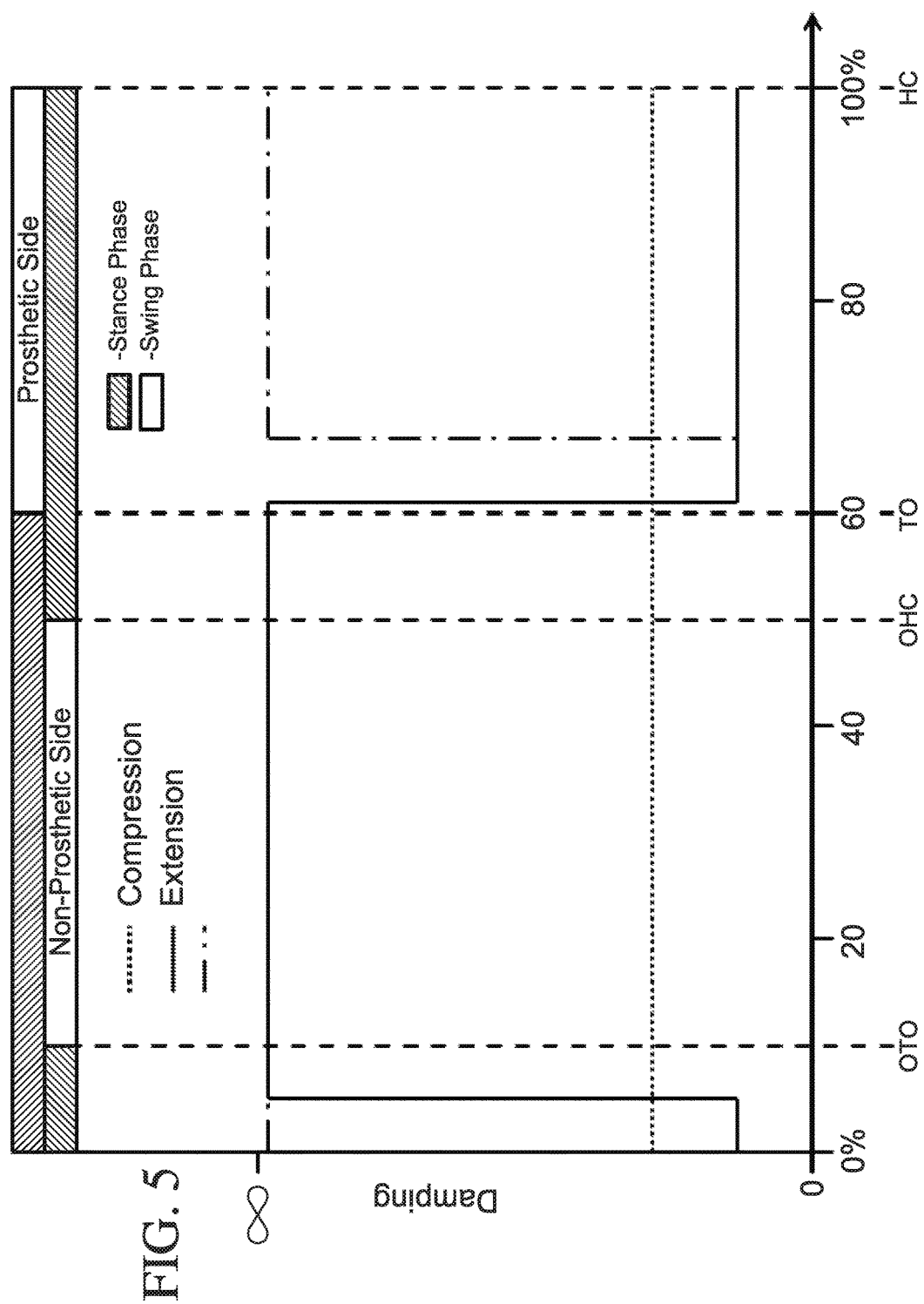
FIG. 5 illustrates a plot of the damping values in each direction for the damper during the gait cycle.

FIG. 5 illustrates a plot of the damping values in each direction for the damper during the gait cycle. In the direction of compression, the damping during walking should be low enough to allow the foot to quickly reach the surface, but not so low that the foot makes a slapping sound when it encounters the surface. The precise value will be dependent on the weight, foot length, and gait mechanics of each individual user and will parallel standard clinical practice for adjusting similar properties of other commercially available components. Ideally the precise amount of damping will be adjustable by the prosthetist for customization to the individual. For long-term standing tasks (doing the dishes, standing at a work station at work, etc.), an ideal embodiment would also be able to raise the compression damping to near infinite (through the use of a cutoff valve) to improve stability when loading the heel, however this function is not of use during walking tasks. The extension damping must be high or nearly infinite (closed cutoff valve, effectively fixing the length of the damper against extension) when the user begins to roll over the foot (in the plot, this is shown as approximately 5% of the gait cycle) and must remain so until the point of toe-off. At the very beginning of swing phase, the cutoff valve is opened, allowing the damper to extend under the load from the spring until the prosthesis has returned to a neutral position (ideally within 0.13 seconds). After the foot has returned to a neutral position for swing phase, the cutoff valve can be closed again. Thus, the cutoff valve could close as early as 0.13 seconds after toe-off or as late as at the moment of foot flat (approximated as 5% of the next gait cycle, but varies by step and surface conditions).

Figure 6:
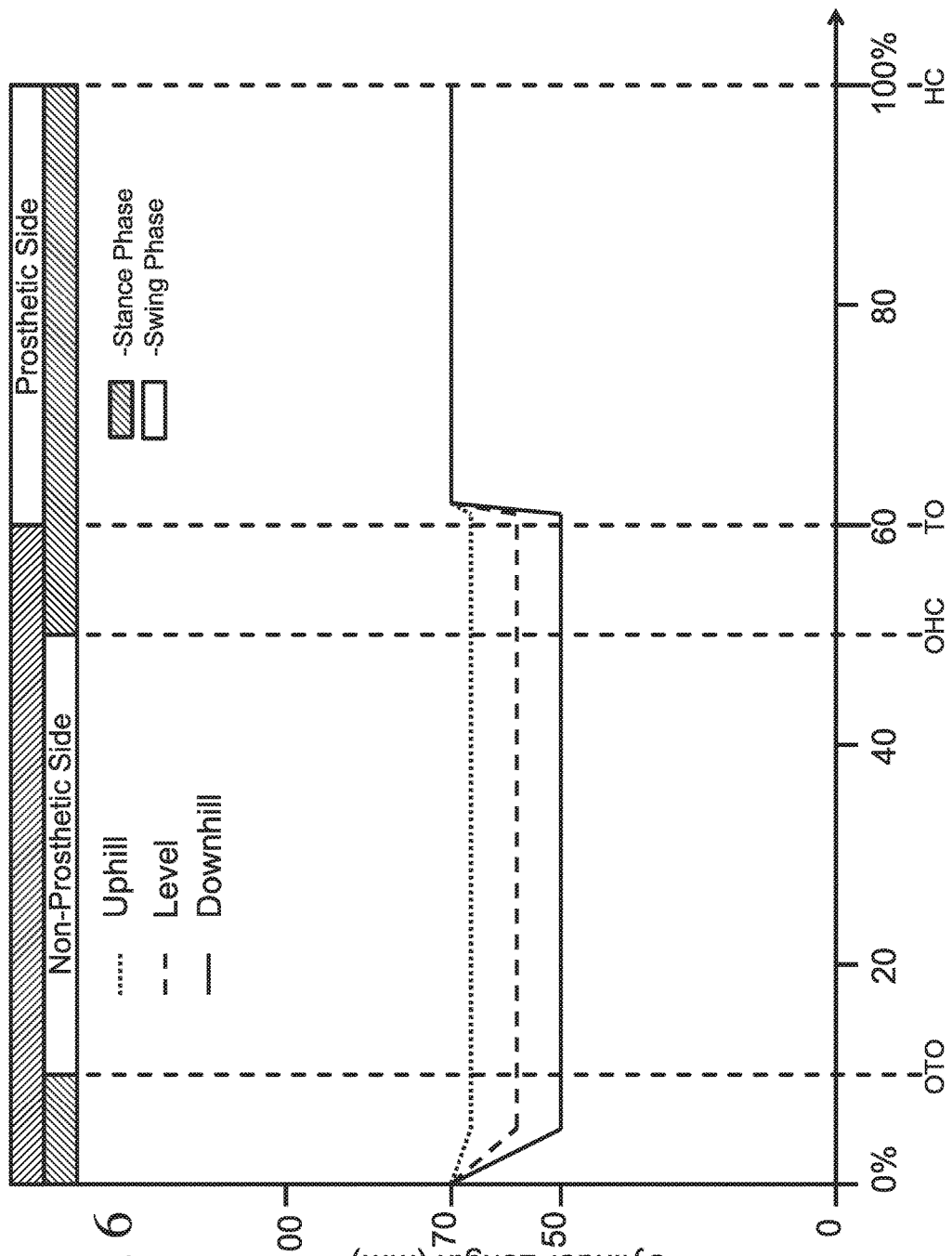
FIG. 6 illustrates a plot of the cylinder (damper) length.

FIG. 6 illustrates a plot of the cylinder (damper) length. The current model of the novel ankle-foot prosthesis has a damper with a fully extended length of 70 mm, and a fully compressed length of 50 mm. This corresponds to a 30-35 degree range of ankle motion. Other designs may use different numbers, however the relationships will still hold. When walking on level ground, the ankle will plantarflex, allowing the foot plate to become flat on the walking surface, during the first approximately 5-10% of the gait cycle. Once the foot is flat on the surface and the user begins to roll over the foot, the damper is unable to extend, so the spring-damper combination remains at its partially extended length throughout the remainder of stance phase. When the prosthesis is lifted from the ground (TO), the cutoff valve is opened and the spring returns the foot to a neutral position for swing phase. When walking uphill, the foot will be flat on the surface in a more dorsiflexed position, so the foot will not plantarflex much during early stance, whereas when walking downhill the foot will plantarflex much more before it is flat on the surface.

Figure 7:
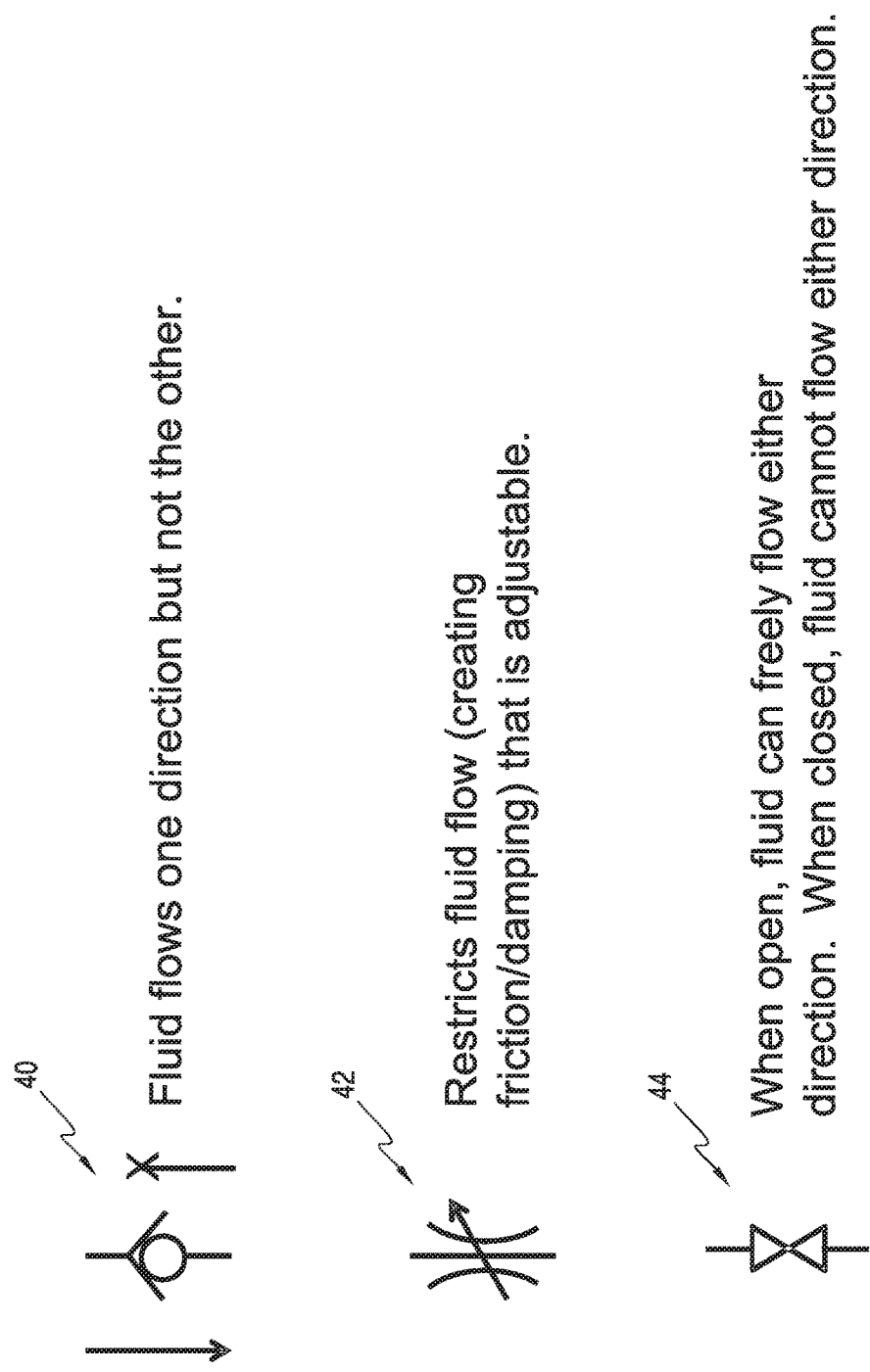
FIG. 7 shows three hydraulic circuit symbols used for fluid circuit schematics shown in FIGS. 8-16.

FIG. 7 shows three hydraulic circuit symbols used for fluid circuit schematics shown in FIGS. 8-16. The symbol used for the check valve 40 is most commonly used to refer to a ball valve, although other types of check valves may also be used. The variable restriction 42 is the damping element of the circuit. There is some damping (fluid resistance) due to friction in the lines and passing through other elements of the circuit, so there is a minimum level of damping regardless. Thus, in some embodiments, the restriction element is not present indicating the use of innate damping alone. The reference numeral 44 designates a cutoff value.

Figure 8:
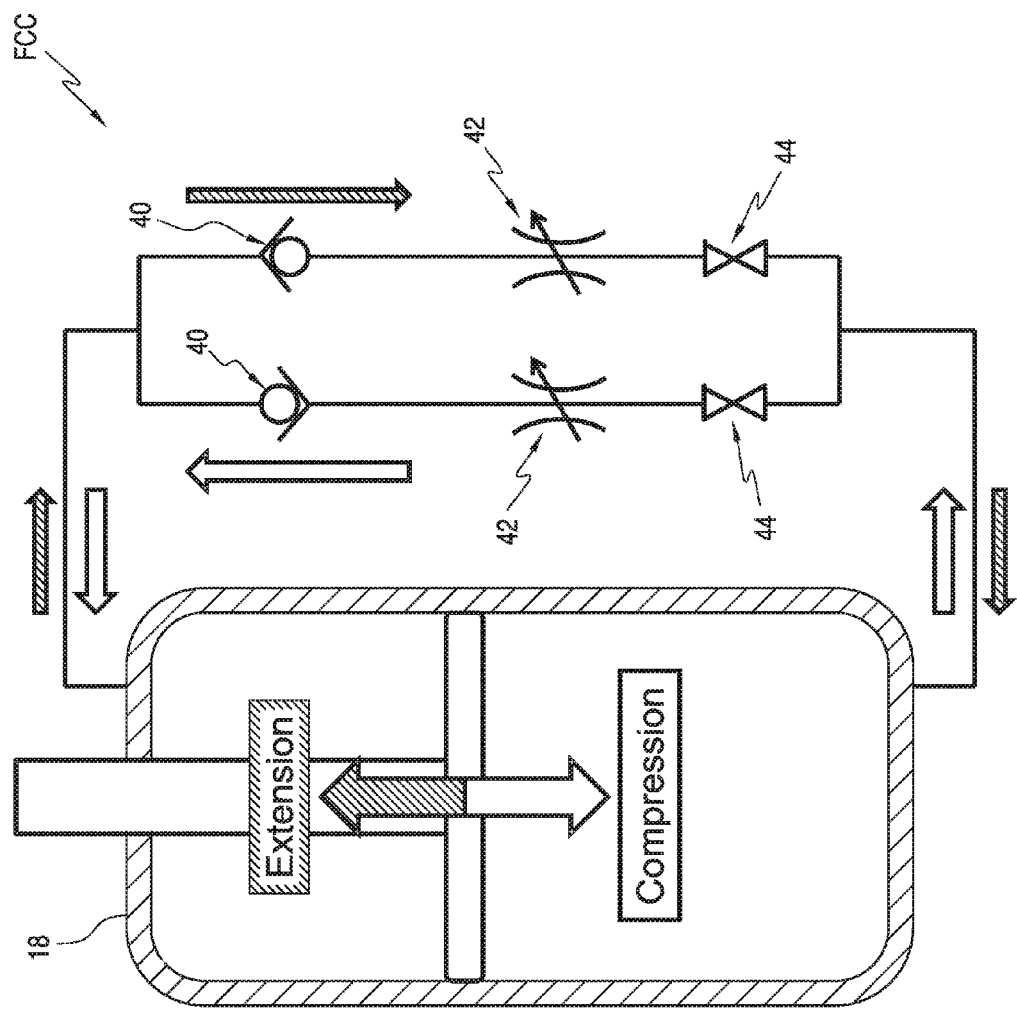
FIGS. 8-16 disclose various preferred embodiments of the fluid control circuit (FCC) used in the present invention.

FIG. 8 discloses the most complex and powerful embodiment of the fluid control circuit (FCC). The fluid circuit splits into two branches. Each branch has a check valve 40 oriented to permit fluid flow in either compression or extension alone, thereby separating the extension and compression properties for the damper. In the compression line, there is provided a variable restriction element 42, where the prosthetist could adjust the damping level to optimize the prosthesis for the individual patient. In the extension line, there is also a variable restriction element 42 that could be adjusted to tune the neutralization damping after toe-off to address any issues with the speed of neutralization or with noises that could arise from underdamped neutralization. Both lines have independent cutoff valves 44, allowing the extension damping to be raised to nearly infinite as appropriate during each step and then both cutoff valves to be closed for standing tasks, making a stable base of support for the user.

Figure 9:
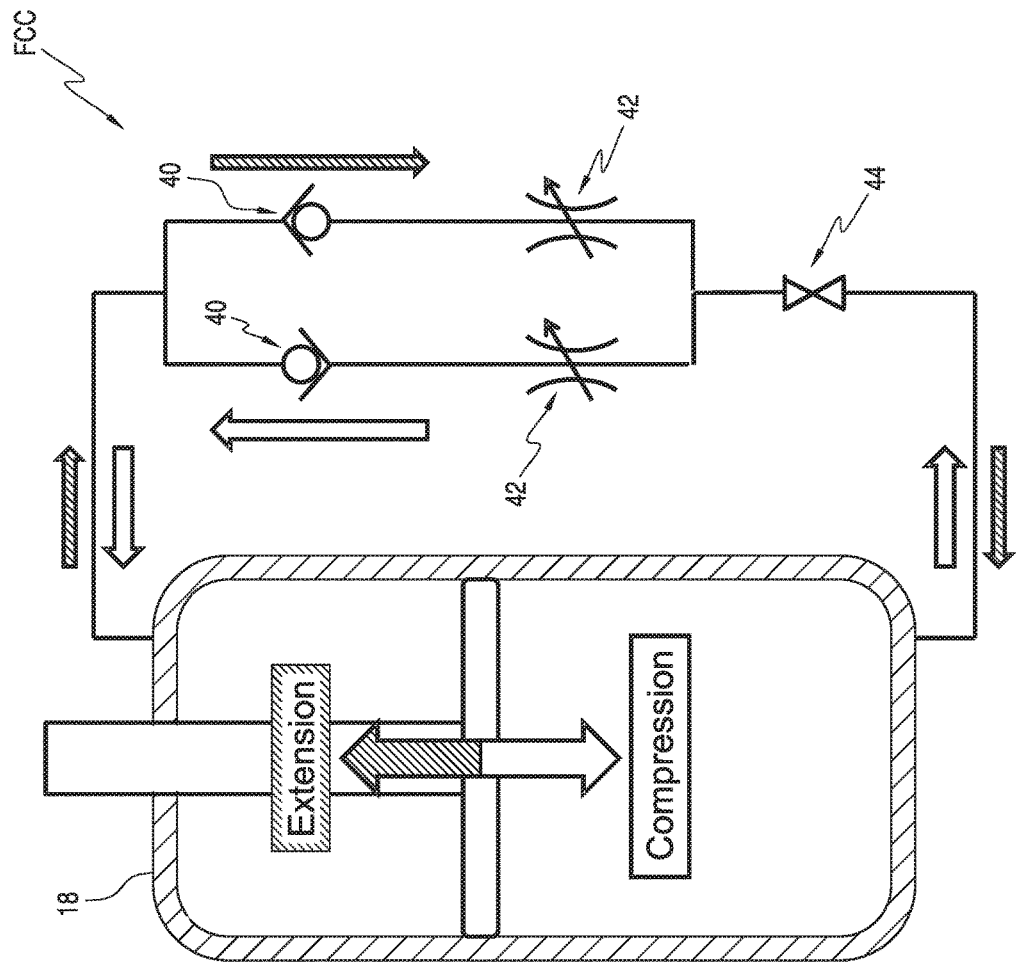

FIG. 9 discloses an embodiment that contains all of the adjustability of the embodiment of FIG. 8, but only a single cutoff valve 44 is used on a common line to arrest both compression and extension of the damper simultaneously. The advantage of this system over FIG. 8 is fewer parts (one fewer cutoff valve). The disadvantage of this system compared with the embodiment of FIG. 8 is that sensors would need to be in place to insure that the cutoff valve would open at the time of toe-off and close at exactly the time of foot flat to prevent unexpected instability and potential falls.

Figure 10:
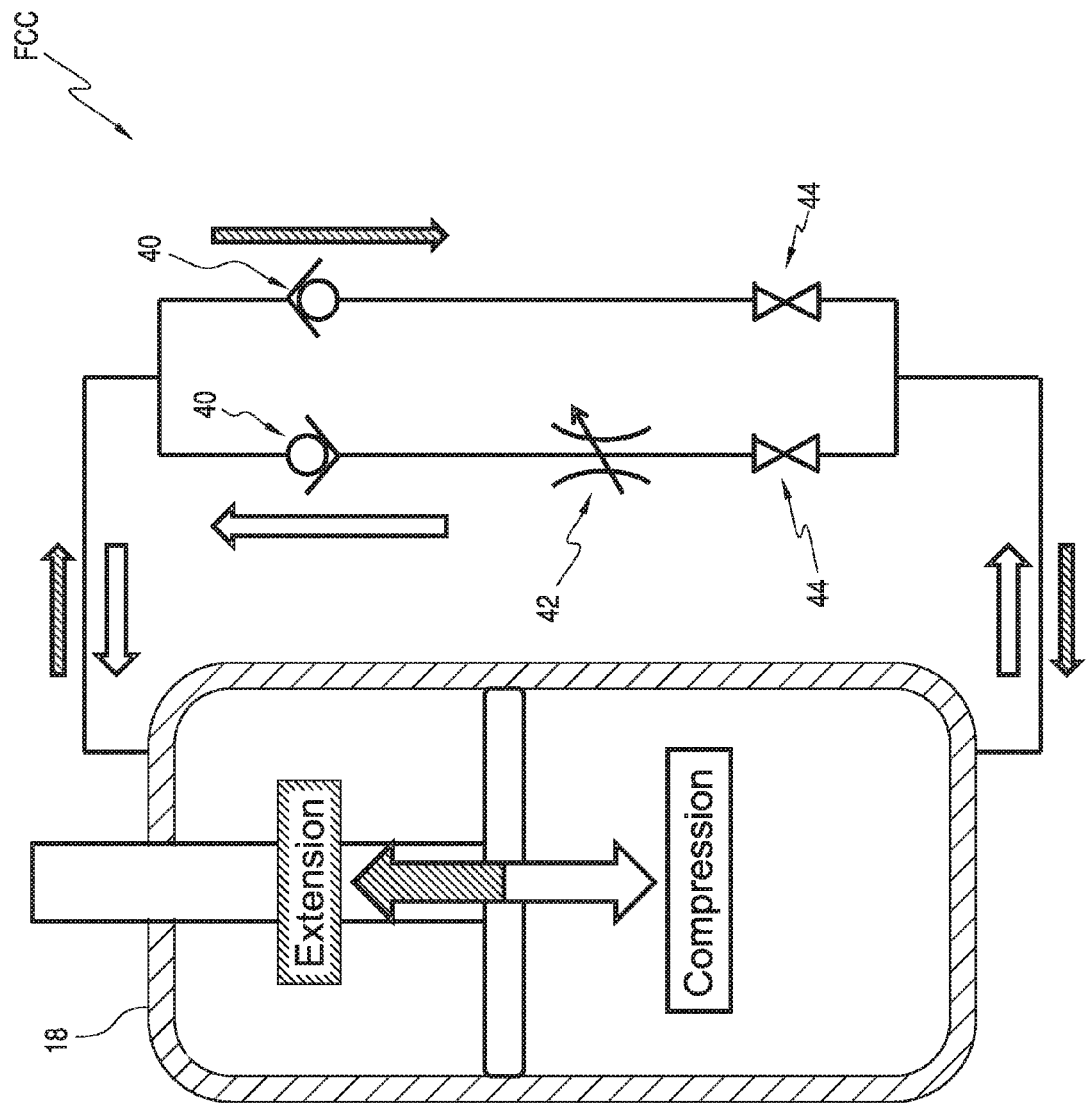

FIG. 10 discloses an embodiment that is similar to the embodiment of FIG. 8, except it does not have a variable restriction element 42 on the extension line. Therefore, there is no way to tune the extension damping for neutralization after toe-off. This embodiment is more efficient because of the reduced number of components (saving weight, size and cost) but only if the fluid circuit can be optimized to allow the foot to return to neutral within 0.13 seconds without oscillating or making loud noises when it reaches the neutral position. This system retains the ability to cutoff both compression and extension for standing tasks.

Figure 11:
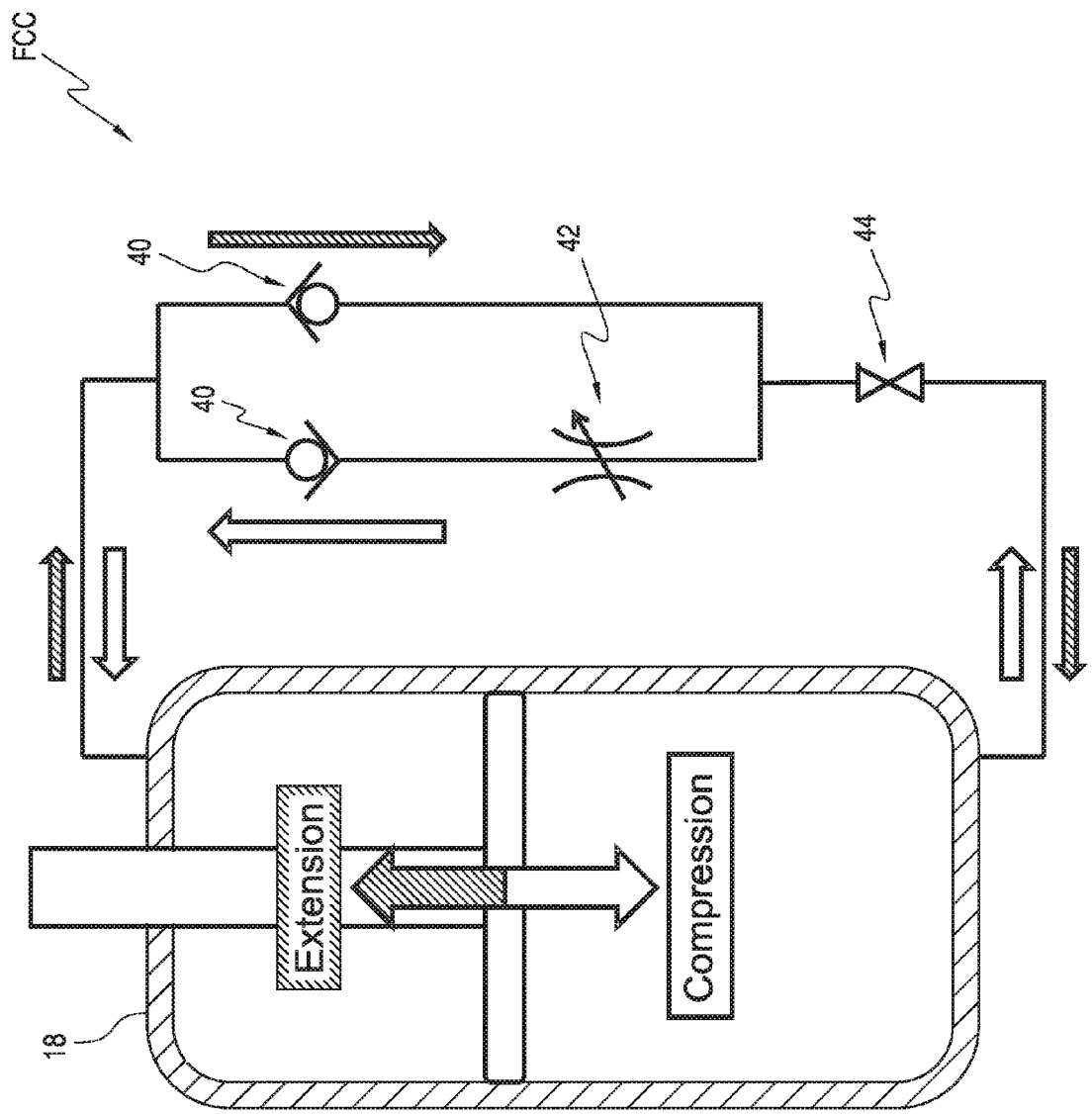

FIG. 11 discloses an embodiment similar to the embodiments presented in both FIGS. 9-10, however, it lacks the ability to adjust extension damping and has a single cutoff valve 44 to arrest motion in both extension and compression simultaneously. This is even more efficient, having removed two components from the system and saving weight, size, and cost. The challenges with this embodiment have been discussed in paragraphs [0039] and [0040].

Figure 12:
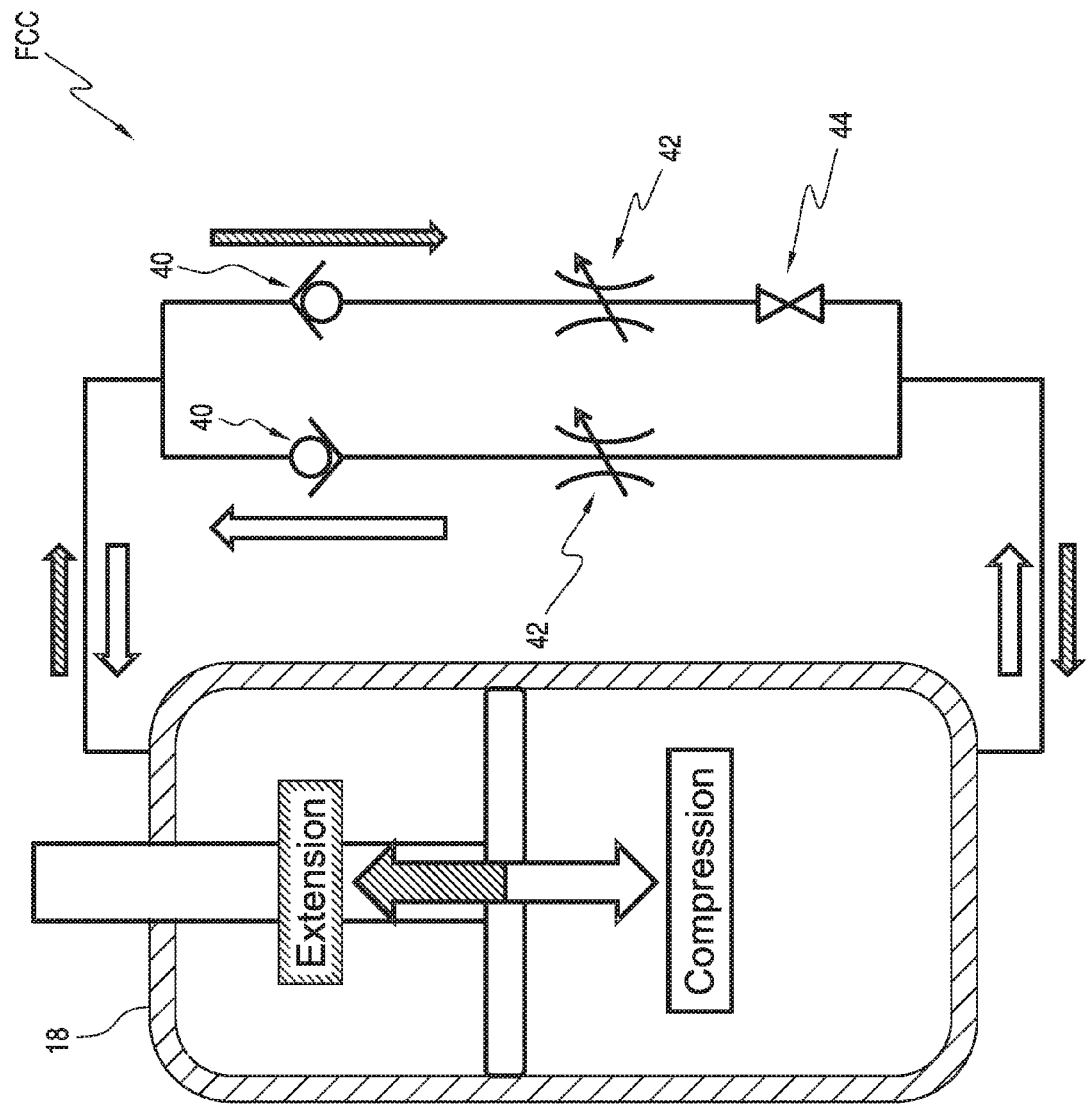

The embodiment of FIG. 12 is similar to the embodiment of FIG. 8, except that it does not have a cutoff valve 44 in the compression line. For this reason, the compression damping will remain constant throughout the gait cycle and compression motion will not be arrested during standing tasks. Both lines have adjustable damping from the variable restriction elements and the extension line still has a cutoff valve. This embodiment could be realized in a purely passive system, where the biomechanics of walking (e.g. load on the prosthesis) control the opening and closing of the cutoff valve. For example, a spring-loaded hinge or telescoping element within the prosthesis could close the cutoff valve when load is applied to the prosthesis and open the cutoff valve when load is removed from the prosthesis. It would not be practical to rely on this type of physical input to control the compression line for standing tasks, so none of the previous embodiments would be practical for purely passive operation.

Figure 13:
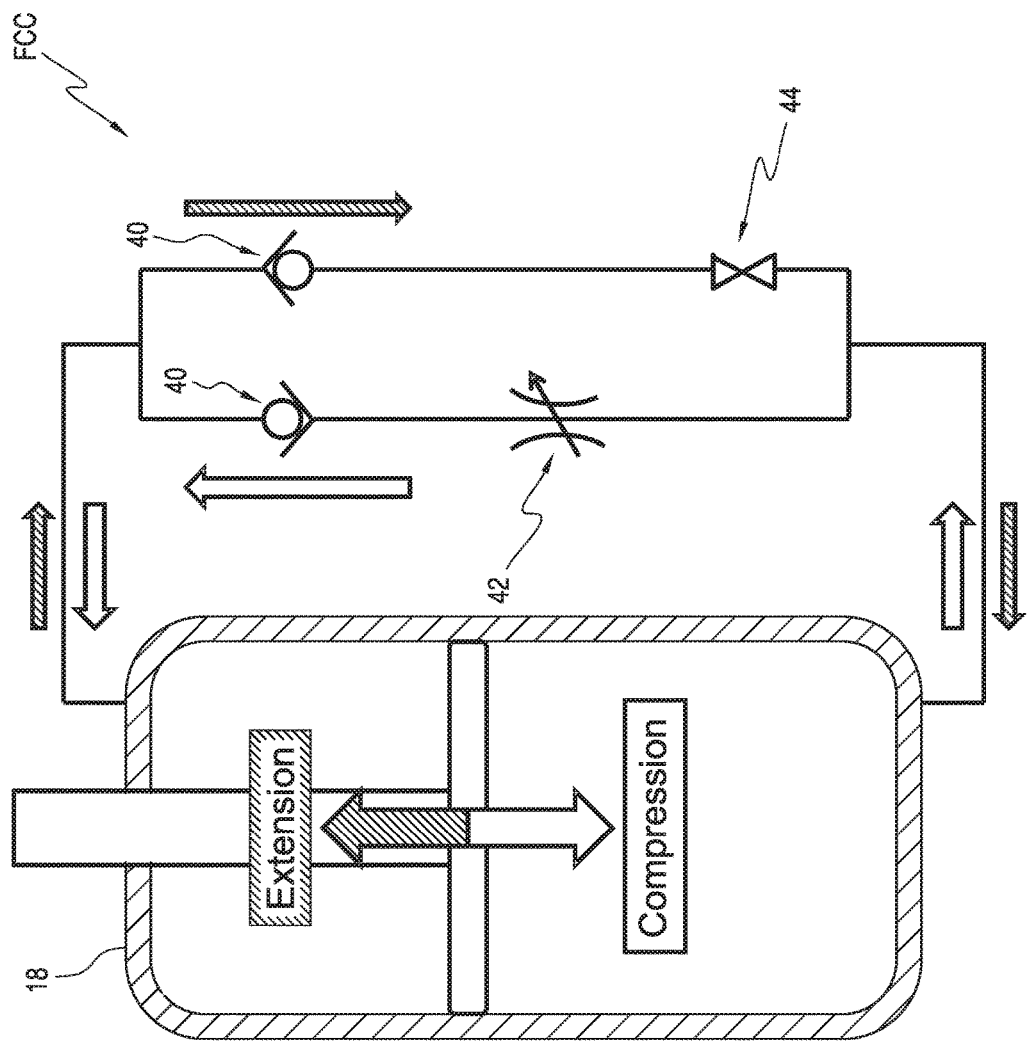

The embodiment of FIG. 13 is similar to the embodiments of FIGS. 10 and 12, however, it also lacks the ability to adjust the damping in the extension line but saves weight, size, and cost. But it lacks the ability to cutoff the compression line and therefore does not have the standing stability feature of the earlier embodiments.

Figure 14:
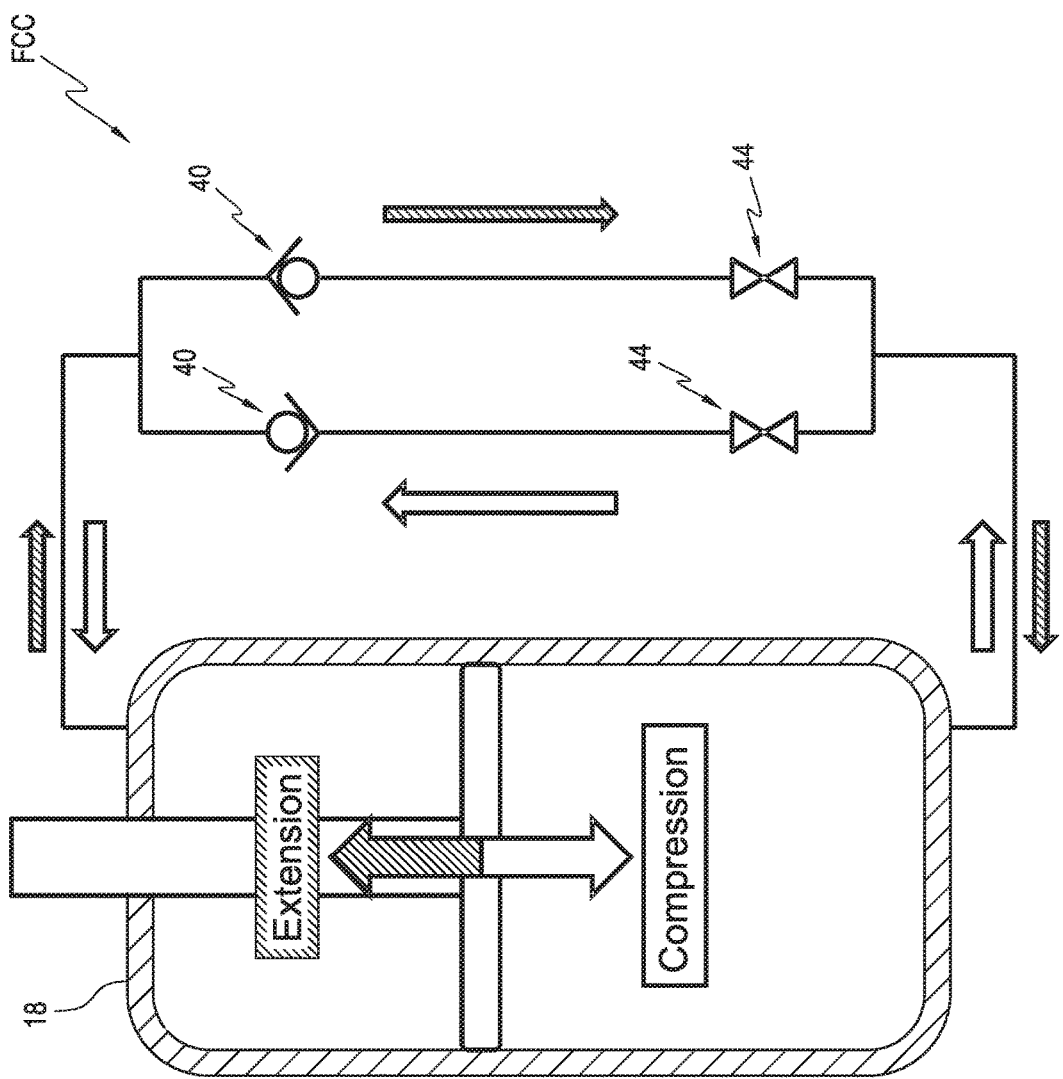

The embodiment of FIG. 14 is similar to the embodiment of FIG. 8, but lacks variable dampers 42. The level of resistance for compression can be adjusted by the prosthetist by changing springs or by pre-compressing the spring. Otherwise the function would be the same.

Figure 15:
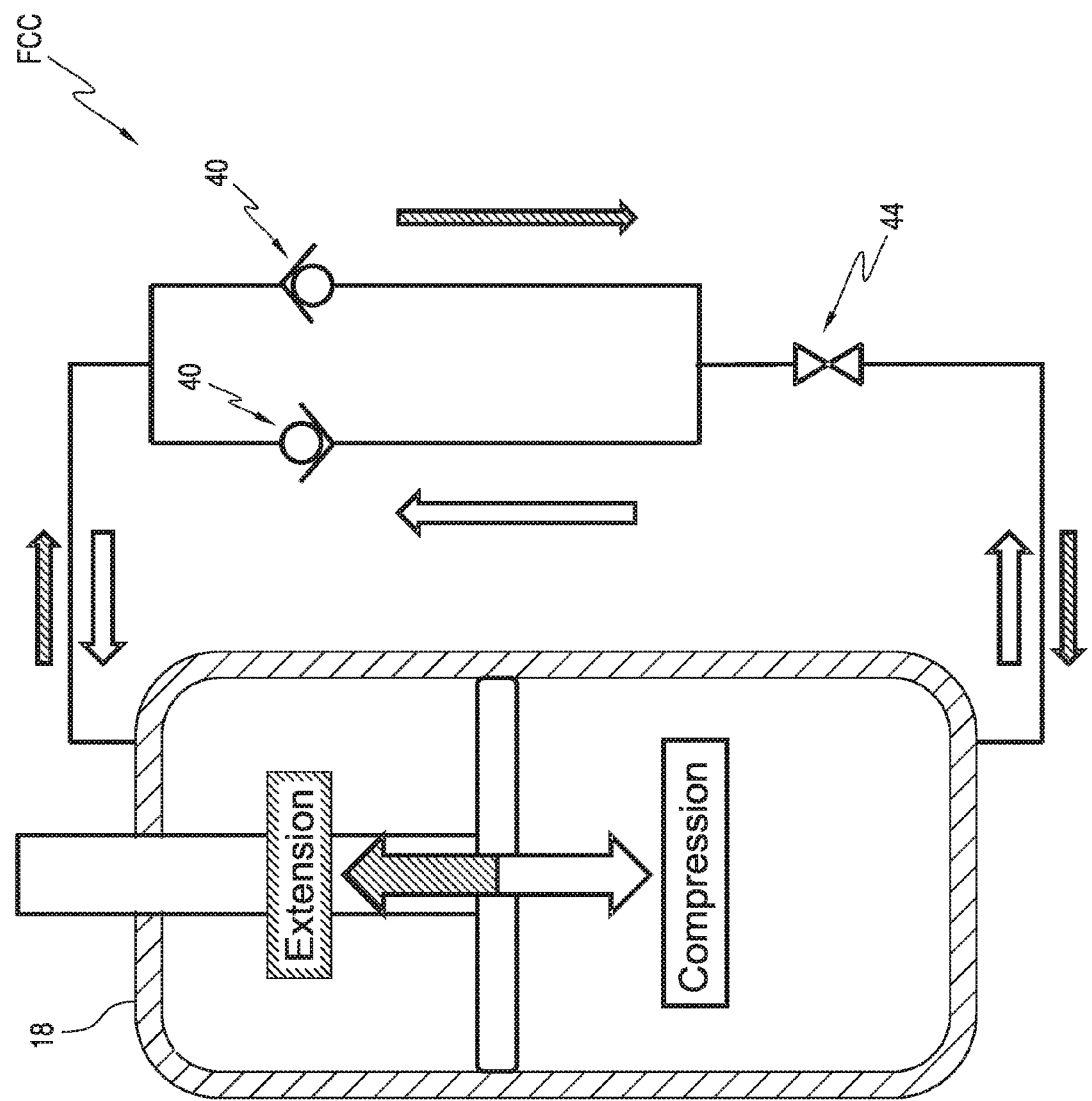

The embodiment of FIG. 15 is similar to the embodiment of FIG. 9, but lacks variable dampers 42. The level of resistance for compression can be adjusted by the prosthetist by changing springs or by pre-compressing the spring.

Figure 16:
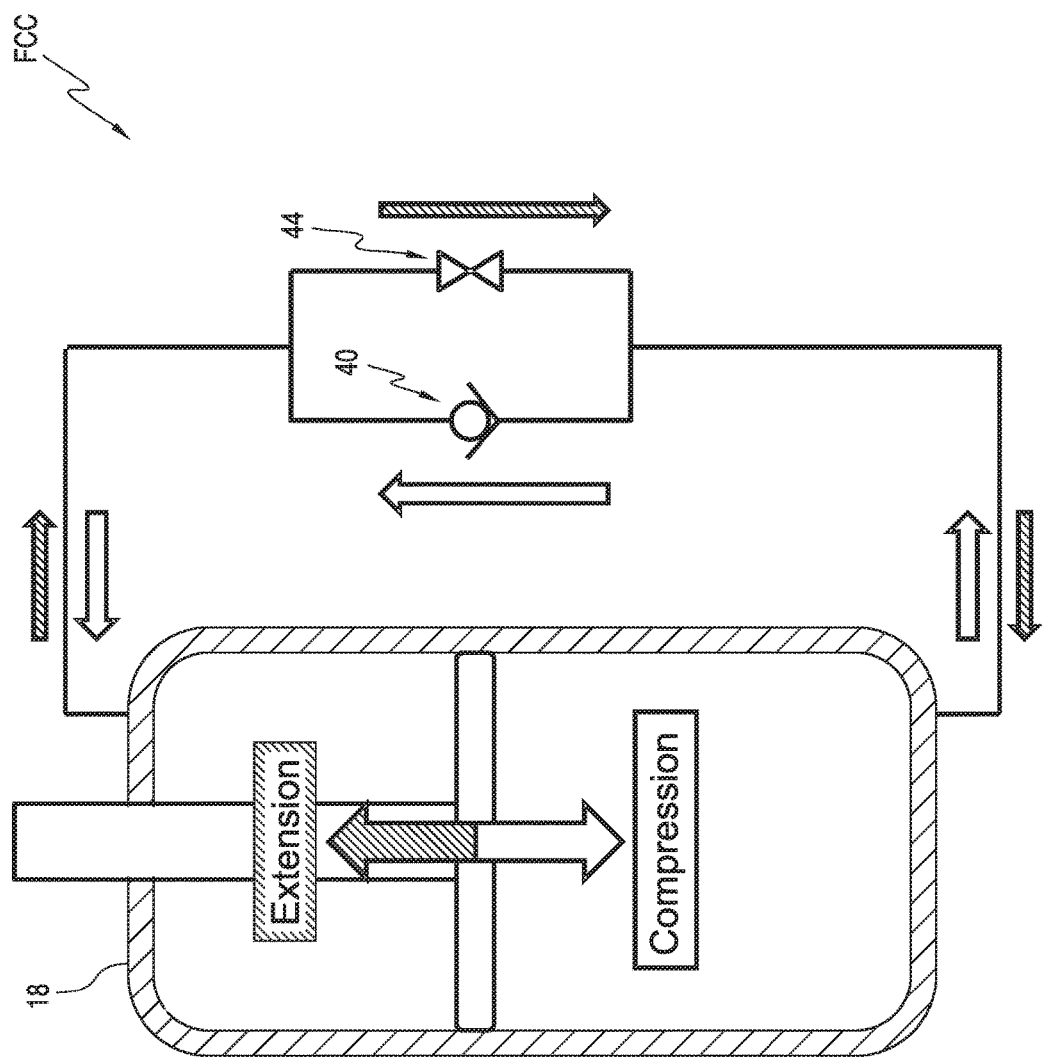

FIG. 16 shows our simplest embodiment. There is a check valve 40 to permit compression, but not extension, and then when the foot is to be neutralized the cutoff valve is opened, permitting extension by bypassing the check valve 40. Ideally the cutoff valve 44 would be mechanically opened and closed by loads applied during the gait cycle, resulting in a purely passive system with no batteries, microprocessors, or other electronic components, though this could be actuated by a solenoid or other actuator and controlled by electronics.

While this invention has been described as having preferred sequences, ranges, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

REFERENCES

The following references, and any cited in the disclosure herein, are hereby incorporated herein in their entirety by reference.
1. Hansen, A., Childress, D., Miff, S., Gard, S., Mesplay, K. (2004) The Human Ankle During Walking: Implications for Design of Biomimetic Ankle Prostheses and Orthoses. Journal of Biomechanics, Vol. 37, No. 10, 1467-1474.
2. Williams R J, Hansen A H, Gard S A. (2009) Prosthetic Ankle-Foot Mechanism Capable of Automatic Adaptation to the Walking Surface. Journal of Biomechanical Engineering, Vol., 131, No. 3, 035002.
3. Hansen A, Brielmaier S, Medvec J, Pike A, Nickel E, Merchak P, Weber M (2012) Prosthetic Foot with Adjustable Stability and its Effects on Balance and Mobility. 38th Annual Meeting and Scientific Symposium of the American Academy of Orthotists and Prosthetists, March 21-24, Atlanta. Ga.
4. Nickel E A, Hansen A H, Gard S A. (2012) Prosthetic Ankle-Foot System that Adapts to Sloped Surfaces. ASME Journal of Medical Devices, Vol. 6, No. 1, 011006.

What is claimed is:
1. An ankle-foot prosthesis, comprising:
 a) a foot plate including a rear portion and a forward deflectable portion;
 b) an ankle frame including anterior and posterior portions and an apex portion;

c) said posterior portion of said ankle frame attached to said rear portion of said foot plate;
d) a yoke pivotally connected to said apex portion of said ankle frame and including a member for attaching to a prosthetic leg;
e) a hydraulic damper having a first end pivotally connected to said yoke and a second end pivotally connected to said posterior portion of said ankle frame;
f) a spring disposed in parallel to said damper;
g) a fluid control circuit for controlling extension and compression of said damper;
h) said anterior portion of said ankle frame including a curved surface inclined upwardly relative to said foot plate and forwardly toward said forward deflectable portion of said foot plate;
i) said curved surface forming a roll-over surface for limiting a dorsiflexion deflection of said forward deflectable portion of said foot plate by a direct engagement therewith;
j) said fluid control circuit including a check valve for only allowing compression of said damper;
k) said fluid control circuit including a cutoff valve for allowing extension of said damper;
l) said cutoff valve allowing extension of said damper during a gait cycle at least between prosthetic side toe off and 0 to 0.13 seconds thereafter; and
m) said cutoff valve allowing extension of said damper during the gait cycle at most between prosthetic side toe off and the next prosthetic side foot flat.

2. The ankle-foot prosthesis of claim 1, further comprising:
a) another check valve positioned in series with said cutoff valve.

3. The ankle-foot prosthesis of claim 2, further comprising:
a) another cutoff valve for allowing compression of said damper during a walking mode and preventing compression of said damper during a standing mode.

4. The ankle-foot prosthesis of claim 1, further comprising:
a) at least one variable fluid-flow resistor for said fluid control circuit for adjusting hydraulic fluid resistance in dorsiflexion, plantarflexion, or both.

5. An ankle-foot prosthesis, comprising:
a) a foot plate including a rear portion and a forward deflectable portion;
b) an ankle frame including anterior and posterior portions and an apex portion;
c) said posterior portion of said ankle frame attached to said rear portion of said foot plate;
d) a yoke pivotally connected to said apex portion of said ankle frame and including a member for attaching to a prosthetic leg;
e) a hydraulic damper having a first end pivotally connected to said yoke and a second end pivotally connected to said posterior portion of said ankle frame;
f) a spring disposed in parallel to said damper;
g) a fluid control circuit for controlling extension and compression of said damper;
h) said anterior portion of said ankle frame including a curved surface inclined upwardly relative to said foot plate and forwardly toward said forward deflectable portion of said foot plate;
i) said curved surface forming a roll-over surface for limiting a dorsiflexion deflection of said forward deflectable portion of said foot plate by a direct engagement therewith;
j) said fluid control circuit including a cutoff valve for preventing compression and extension of said damper at prosthetic side foot between prosthetic side foot flat and prosthetic side toe off during a walking mode of a gait cycle;
k) said cutoff valve allowing compression and extension of said damper between prosthetic side toe off until prosthetic side foot flat during the walking mode of the gait cycle; and
l) said cutoff valve preventing compression and extension of said damper during a standing mode.

6. The ankle-foot prosthesis of claim 5, further comprising:
a) at least one check valve for said fluid control circuit for allowing compression of said damper.

7. The ankle-foot prosthesis of claim 5, further comprising:
a) at least one check valve for said fluid control circuit for allowing extension of said damper.

8. The ankle-foot prosthesis of claim 6, further comprising:
a) at least one variable fluid-flow resistor for said fluid control circuit for adjusting hydraulic fluid resistance in dorsiflexion, plantarflexion, or both.

9. An ankle-foot prosthesis, comprising:
a) a foot plate including a rear portion and a forward deflectable portion;
b) an ankle frame including anterior and posterior portions and an apex portion;
c) said posterior portion of said ankle frame attached to said rear portion of said foot plate;
d) a yoke pivotally connected to said apex portion of said ankle frame and including a member for attaching to a prosthetic leg;
e) a hydraulic damper having a first end pivotally connected to said yoke and a second end pivotally connected to said ankle frame;
f) a spring disposed in parallel to said damper;
g) a fluid control circuit for controlling extension and compression of said damper;
h) said anterior portion of said ankle frame including a curved surface inclined upwardly relative to said foot plate and forwardly toward said forward deflectable portion of said foot plate; and
i) said curved surface forming a roll-over surface for limiting a dorsiflexion deflection of said forward deflectable portion of said foot plate by a direct engagement therewith.

10. The ankle-foot prosthesis of claim 9, wherein:
a) said fluid control circuit includes a check valve for only allowing compression of said damper.

11. The ankle-foot prosthesis of claim 9, wherein:
a) said fluid control circuit includes a cutoff valve for allowing extension of said damper.

12. The ankle-foot prosthesis of claim 11, wherein:
a) said cutoff valve allows extension of said damper during a gait cycle at least between prosthetic side toe off and 0 to 0.13 seconds thereafter.

13. The ankle-foot prosthesis of claim 11, wherein:
a) said cutoff valve allows extension of said damper during the gait cycle at most between prosthetic side toe off and the next prosthetic side foot flat.

14. The ankle-foot prosthesis of claim 9, wherein:
a) said fluid control circuit includes a cutoff valve for preventing compression and extension of said damper at prosthetic side foot between prosthetic side foot flat and prosthetic side toe off during a walking mode of a gait cycle.

15. The ankle-foot prosthesis of claim 14, wherein:
a) said cutoff valve allows compression and extension of said damper between prosthetic side toe off until prosthetic side foot flat during the walking mode of the gait cycle.

16. The ankle-foot prosthesis of claim 15, wherein:
a) said cutoff valve prevents compression and extension of said damper during a standing mode.

17. The ankle-foot prosthesis of claim 9, wherein:
a) said fluid control circuit includes a check valve for only allowing extension of said damper; and
b) said cutoff valve opens or closes by a load applied to the ankle-foot prosthesis during walking.

18. The ankle-foot prosthesis of claim 17, further comprising:
a) an actuator operating with the load to open or close said cutoff valve.

19. The ankle-foot prosthesis of claim 18, wherein:
a) said actuator comprises a spring-loaded hinge.

20. The ankle-foot prosthesis of claim 18, wherein:
a) said actuator comprises a telescoping element.

* * * * *